US005981842A

United States Patent [19]
Wu et al.

[11] Patent Number: 5,981,842
[45] Date of Patent: Nov. 9, 1999

[54] PRODUCTION OF WATER STRESS OR SALT STRESS TOLERANT TRANSGENIC CEREAL PLANTS

[75] Inventors: Ray J. Wu, Ithaca, N.Y.; Tuan-Hua D. Ho, Chesterfield, Mo.

[73] Assignees: Cornell Research Foundation, Inc., Ithaca, N.Y.; Washington University, St. Louis, Mo.

[21] Appl. No.: 08/730,659

[22] Filed: Oct. 11, 1996

Related U.S. Application Data

[60] Provisional application No. 60/005,223, Oct. 12, 1995.

[51] Int. Cl.$^6$ .......................... C12N 15/29; C12N 15/82; A01H 4/00; A01H 5/00
[52] U.S. Cl. .......................... 800/298; 800/295; 800/278; 800/320; 800/320.1; 800/320.2; 435/320.1; 435/419; 435/468; 536/24.1; 536/23.6
[58] Field of Search .................................... 800/205, 250, 800/DIG. 57, DIG. 55, 295, 298, 278, 320, 320.1, 320.2; 435/172.3, 320.1, 410, 419, 468; 536/24.1, 23.6

[56] References Cited

U.S. PATENT DOCUMENTS

| | | |
|---|---|---|
| 5,097,025 | 3/1992 | Benfey et al. . |
| 5,139,954 | 8/1992 | Litts et al. . |
| 5,256,558 | 10/1993 | Coruzzi et al. . |
| 5,276,269 | 1/1994 | Raikhel . |
| 5,405,765 | 4/1995 | Vasil et al. . |
| 5,422,108 | 6/1995 | Mirkov et al. . |
| 5,428,146 | 6/1995 | Logemann et al. . |
| 5,436,391 | 7/1995 | Fujimoto et al. . |
| 5,489,520 | 2/1996 | Adams et al. . |
| 5,550,318 | 8/1996 | Adams et al. . |

FOREIGN PATENT DOCUMENTS

| | | |
|---|---|---|
| 0 359 617 A2 | 3/1990 | European Pat. Off. . |
| WO 91/02071 | 2/1991 | WIPO . |
| WO 94/10831 | 5/1994 | WIPO . |

OTHER PUBLICATIONS

Gordon–Kamm et al. Transformation of maize cells and regeneration of fertile transgenic plants. The Plant Cell, vol. 2, 603–618, Jul. 1990.

Ried et al. Group 3 late embryogenesis abundant proteins in desiccation–tolerant seedlings of wheat. Plant Physiol. (Jan. 1993) 102: 125–131.

Iturriga et al. Exprission of desiccation–related proteins from the resurrectionplant Craterostigma plantagineum in transgenic tobacco. Plant Molecular Biology 20: 555–558, 1992.

Hong et al. Cloning and characterization of a cDNA encoding a mRNA rapidly–induced by ABA in barley aleurone layers. Plant Molecular Biology 11: 495–506, 1988.

Shimamoto et al., "Fertile Transgenic Rice Plants Regenerated from Transformed Protoplasts," *Nature*, 338:274–76 (1989).

Dure et al., "Common Amino Acid Sequence Domains Among the LEA Proteins of Higher Plants," *Plant Molecular Biology*, 12:475–486 (1989).

Skriver et al., "Gene Expression in Response to Abscisic Acid and Osmotic Stress," *The Plant Cell*, 2:503–512 (1996).

Dure, "A Repeating 11–Mer Amino Acid Motif and Plant Desiccation," *The Plant Journal*, 3:363–369 (1993).

Fitzpatrick, "Pleiotropic Gene Found In Barley Plant," *Genetic Engineering News*, 13(5):1,22 (Mar. 1, 1993).

Lane et al., "Germin, a Protein Marker of Early Plant Development, Is an Oxalate Oxidase," *The Journal of Biological Chemistry*, 268: 12239–12241 (1993).

Chandler, et al., "Gene Expression Regulated By Abscisic Acid and Its Relation to Stress Tolerance," *Annu. Rev. Plant Physiol. Mol.* 45:113–141 (1994).

Straub et al., "Structure and Promoter Analysis of an ABA–and Stress–Regulated Barley Gene, HVA1," *Plant Molecular Biology*, 26:617–630(1994).

Vilardell et al., "Regulation of the rab17 Gene Promoter in Transgenic Arabidopsis Wild–Type, ABA–Deficient and ABA–Insensitive Mutants," *Plant Molecular Biology*, 24:561–569 (1994).

Ishitani et al., "Expression of the Betaine Aldehyde Dehydrogenase Gene in Barley in Response to Osmotic Stress and Absicsic Acid," *Plant Molecular Biology*, 27:307–315 (1995).

Moons et al., "Molecular and Physiological Responses to Abscisic Acid Salts in Roots of Salt–Sensitive and Salt–Tolerant Indica Rice Varieties," *Plant Physiol.*, 107:177–186 (1995).

Silhavy et al., "Isolation and Characterization of a Water–Stress–Inducible cDNA Clone from *Solanum chacoense*," *Plant Molecular Biology*, 27:587–595 (1995).

*Primary Examiner*—Lynette F. Smith
*Assistant Examiner*—Thomas Haas
*Attorney, Agent, or Firm*—Nixon Peabody LLP

[57] ABSTRACT

The present invention is directed to a method of producing a cereal plant cell or protoplast useful for regeneration of a water stress or salt stress tolerant cereal plant by transforming the cereal plant cell or protoplast with a nucleic acid encoding a late embryogenesis abundant protein. A transgenic cereal plant or cereal plant cell or protoplast transformed with a nucleic acid encoding a late embryogenesis abundant protein is also provided. An LEA protein gene, HVA1, from barley (*Hordeum vulgare* L.) was transformed into rice (*Oryza sativa* L.) plants. The resulting transgenic rice plants accumulate the HVA1 protein in both leaves and roots. Transgenic rice plants showed significantly increased tolerance to water stress (drought) and salt stress.

32 Claims, 1 Drawing Sheet

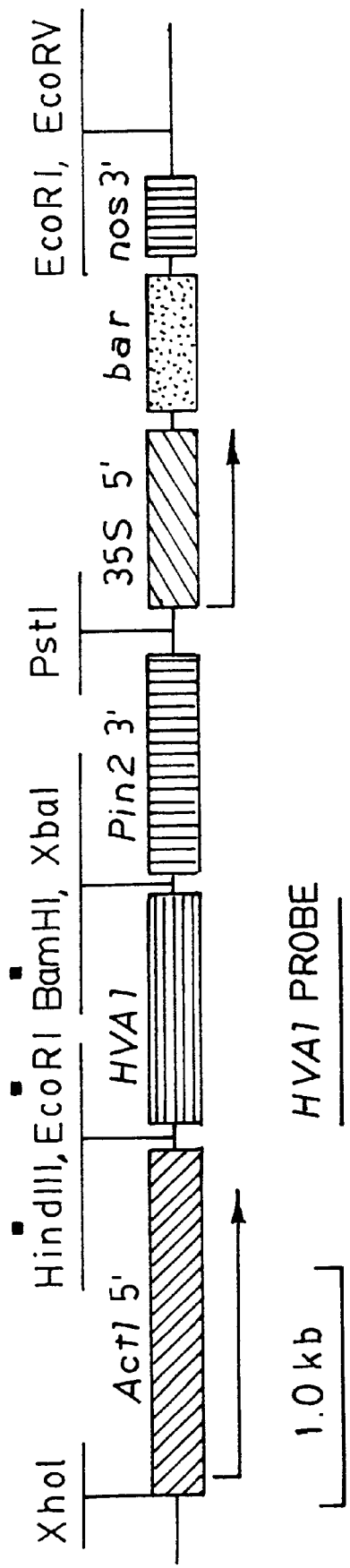

PRODUCTION OF WATER STRESS OR SALT STRESS TOLERANT TRANSGENIC CEREAL PLANTS

This application claims priority of U.S. Provisional Patent Application No. 60/005,223, filed Oct. 12, 1995.

FIELD OF THE INVENTION

The present invention relates generally to transgenic cereal plants, and more particularly to transgenic cereal plants which comprise nucleic acid encoding a late embryogenesis abundant protein which confers water stress or salt stress tolerance on the transgenic cereal plants.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Environmental stresses, such as drought, increased salinity of soil, and extreme temperature, are major factors in limiting plant growth and productivity. The worldwide loss in yield of three major cereal crops, rice, maize (corn), and wheat due to water stress (drought) has been estimated to be over ten billion dollars annually. Breeding of stress-tolerant crop cultivars represents a promising strategy to tackle these problems (Epstein et al., 1980). However, conventional breeding is a slow process for generating crop varieties with improved tolerance to stress conditions. Limited germplasm resources for stress tolerance and incompatibility in crosses between distantly related plant species are additional problems encountered in conventional breeding. Recent progress in plant genetic transformation and availability of potentially useful genes characterized from different sources make it possible to generate stress-tolerant crops using transgenic approaches (Tarczynski et al., 1993; Pilon-Smits et al., 1995).

Characterization and cloning of plant genes that confer stress tolerance remains a challenge. Genetic studies revealed that tolerance to drought and salinity in some crop varieties is principally due to additive gene effects (Akbar et al., 1986a, 1986b). However, the underlying molecular mechanism for the tolerance has never been revealed. Physiological and biochemical responses to high levels of ionic or nonionic solutes and decreased water potential have been studied in a variety of plants. Based on accumulated experimental observations and theoretical consideration, one suggested mechanism that may underlie the adaptation or tolerance of plants to osmotic stresses is the accumulation of compatible, low molecular weight osmolytes such as sugar alcohols, special amino acids, and glycinebetaine (Greenway and Munns, 1980; Yancey et al., 1982). Recently, a transgenic study has demonstrated that accumulation of the sugar alcohol mannitol in transgenic tobacco conferred protection against salt stress (Tarczynski et al., 1993). Two recent studies using a transgenic approach have demonstrated that metabolic engineering of the glycinebetaine biosynthesis pathway is not only possible but also may eventually lead to production of stress-tolerant plants (Holmstrom et al., 1994; Rathinasabapathi et al., 1994).

In addition to metabolic changes and accumulation of low molecular weight compounds, a large set of genes is transcriptionally activated which leads to accumulation of new proteins in vegetative tissue of plants under osmotic stress conditions (Skriver and Mundy, 1990; Chandler and Robertson, 1994). The expression levels of a number of genes have been reported to be correlated with desiccation, salt, or cold tolerance of different plant varieties of the same species. It is generally assumed that stress-induced proteins might play a role in tolerance, but direct evidence is still lacking, and the functions of many stress-responsive genes are unknown. Elucidating the function of these stress-responsive genes will not only advance our understanding of plant adaptation and tolerance to environmental stresses, but also may provide important information for designing new strategies for crop improvement (Chandler and Robertson, 1994).

Late embryogenesis abundant proteins (LEA proteins) were first characterized in cotton as a set of proteins that are highly accumulated in the embryos at the late stage of seed development (Dure et al., 1981). Subsequently, many LEA proteins or their genes have been characterized from different plant species (collated by Dure, 1992). Based on their common amino acid sequence domains, LEA proteins were classified into three major groups (Baker et al., 1988; Dure et al., 1989). A group 2 LEA protein and its cDNA have been characterized from rice (Mundy and Chua, 1988). The four members of a group 2 LEA gene family are tandemly arranged in a single locus, and are coordinately expressed in various rice tissues in response to ABA, drought, and salt stress (Yamaguchi-Shinozaki et al., 1989). However, the functions of these LEA proteins are unknown. Recently, both group 2 and group 3 LEA proteins have been characterized from Indica rice varieties and the accumulation of these LEA proteins in response to salt stress were correlated with varietal tolerance to salt stress (Moons et al., 1995). Group 2 LEA proteins (dehydrins) containing extensive consensus sequence were detected in a wide range of plants, both monocots and dicots (Close et al., 1993). A recent study showed that a group 2 LEA gene is present in many plant species but the expression of this gene is differentially regulated in stress sensitive and tolerant species (Danyluk et al., 1994).

A barley group 3 LEA protein, HVA1, was previously characterized from barley aleurone. The HVA1 gene is specifically expressed in the aleurone layers and the embryos during late stage of seed development, correlating with the seed desiccation stage (Hong et al., 1988). Expression of the HVA1 gene is rapidly induced in young seedlings by ABA and several stress conditions including dehydration, salt, and extreme temperature (Hong et al., 1992).

HVA1 protein belongs to the group 3 LEA proteins that include other members such as wheat pMA2005 (Curry et al., 1991; Curry and Walker-Simmons, 1993), cotton D-7 (Baker et al., 1988), carrot Dc3 (Seffens et al., 1990), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988; Dure et al., 1988; Dure, 1993). The barley HVA1 gene and the wheat pMA2005 gene (Curry et al., 1991; Curry and Walker-Simmons, 1993) are highly similar at both the nucleotide level and predicted amino acid level. These two monocot genes are closely related to the cotton D-7 gene (Baker et al., 1988) and carrot Dc3 gene (Seffens et al., 1990) with which they share a similar structural gene organization (Straub et al., 1994).

In many cases, the timing of LEA mRNA and protein accumulation is correlated with the seed desiccation process and associated with elevated in vivo abscisic acid (ABA) levels. The expression of LEA genes is also induced in isolated immature embryos by ABA, and in vegetative tissues by ABA and various environmental stresses, such as drought, salt, and extreme temperature (Skriver and Mundy, 1990; Chandler and Robertson, 1994).

There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons et al., 1995).

On the other hand, the presence of other LEA proteins is not always correlated with stress tolerance. For example, comparative studies on wild rice and paddy rice showed that the intolerance of wild rice seeds to dehydration at low temperature is not due to an absence of or an inability to synthesize group 2 LEA/dehydrin proteins, ABA, or soluble carbohydrates (Bradford and Chandler, 1992; Still et al., 1994). Overproduction of a group 2 LEA protein from the resurrection plant Craterostigma in tobacco did not confer tolerance to osmotic stress (Iturriaga et al., 1992). It has been found that LEA proteins are not sufficient to confer desiccation tolerance in soybean seeds, and it is the LEA proteins together with soluble sugars that contribute to the tolerance (Blackman et al., 1991, 1992).

In these reported cases of increased water stress or salt stress tolerance, a large set of genes has been activated in the stressed plant (Skriver and Mundy, 1990; Chandler and Robertson, 1994). The LEA protein(s) are the product of just one of these gene(s), and many other proteins are also correlated with the increased water stress or salt stress tolerance (i.e. levels of these other proteins also increase in response to water stress or salt stress). Therefore, although a correlation exists between LEA proteins and increased water stress or salt stress tolerance, no evidence exists that any of the particular activated genes (including the LEA genes) can confer water stress or salt stress tolerance upon a plant. Accordingly, identification of appropriate genes for use in genetic engineering of plants to increase water stress or salt stress tolerance has not been attained.

A need exists, therefore, for the identification of a gene encoding a protein that can confer water stress or salt stress tolerance on a plant transformed with the gene. Such a water stress or salt stress tolerant plant can find many uses, particularly in agriculture and particularly in regard to cereal plants which are a major crop plant.

SUMMARY OF INVENTION

To this end, the subject invention provides a method of producing a cereal plant cell or protoplast useful for regeneration of a water stress or salt stress tolerant cereal plant by transforming a cereal plant cell or protoplast with a nucleic acid encoding a late embryogenesis abundant protein.

The invention further provides a cereal plant cell or protoplast transformed with a nucleic acid encoding a late embryogenesis abundant protein that confers water stress or salt stress tolerance on a cereal plant regenerated from the cereal plant cell or protoplast, as well as a transgenic cereal plant transformed with a nucleic acid encoding a late embryogenesis abundant protein that confers water stress or salt stress tolerance to the plant.

The invention also provides seed produced by the transgenic cereal plants according to the subject invention, and seed which, upon germination, produces the transgenic cereal plants of the subject invention.

The invention additionally provides a method of increasing tolerance of a cereal plant to water stress or salt stress conditions. The method comprises increasing levels of a late embryogenesis abundant protein in the cereal plant. This can be accomplished by introducing a promoter and a nucleic acid encoding a late embryogenesis abundant protein (LEA) by transforming the cereal plant.

More particularly, an LEA protein gene, HVA1, from barley (*Hordeum vulgare* L.) was transformed into rice (*Oryza sativa* L.) plants. The resulting transgenic rice plants constitutively accumulate the HVA1 protein in both leaves and roots. Transgenic rice plants showed significantly increased tolerance to water stress (drought) and salt stress. The increased tolerance was reflected by the delayed development of damage symptoms caused by stress and the improved recovery upon the removal of the stress conditions. The extent of increased stress tolerance was correlated with the level of the HVA1 protein accumulated in the transgenic rice plants. Thus, LEA genes can be used as molecular tools for genetic crop improvement by conferring stress tolerance.

BRIEF DESCRIPTION OF THE DRAWINGS

These and other features and advantages of this invention will be evident from the following detailed description of preferred embodiments when read in conjunction with the accompanying drawing in which:

FIG. 1 shows the structure of the plasmid pBY520 for expression of HVA1 in transgenic rice. Only common restriction endonuclease sites are indicated and those sites used for DNA digestion in DNA blot hybridization are marked with a filled square. The DNA fragment used as a probe in DNA blot hybridization is also indicated.

DETAILED DESCRIPTION

The invention provides a method of producing a cereal plant cell or protoplast useful for regeneration of a water stress or salt stress tolerant cereal plant by transforming a cereal plant cell or protoplast with a nucleic acid encoding a late embryogenesis abundant protein. Once transformation has occurred, the cereal plant cell or protoplast can be regenerated to form a transgenic cereal plant.

The invention is also directed to a method of increasing tolerance of a cereal plant to water stress or salt stress conditions. The method comprises increasing levels of a late embryogenesis abundant protein in the cereal plant. This can be accomplished by controlling expression of a heterologous late embryogenesis abundant protein gene with a strong promoter in the cereal plant.

Cereal which can be transformed in accordance with the subject invention are members of the family Gramineae (also known as Poaceae), and include rice (genus Oryza), wheat, corn, barley, oat, sorghum, and millet. Preferably, the cereal is rice, wheat, or corn, and most preferably the cereal is rice. Many species of cereals can be transformed, and within each species the numerous subspecies and varieties can be transformed. For example, within the rice species is subspecies Indica rice (*Oryza sativa* ssp. Indica), which includes the varieties IR36, IR64, IR72, Pokkali, Nona Bokra, KDML105, Suponburi 60, Suponburi 90, Basmati 385, and Pusa Basmati 1. Another rice subspecies is Japonica, which includes Nipponbere, Kenfeng and Tainung 67. Examples of suitable maize varieties include A188, B73, VA22, L6, L9, K1, 509, 5922, 482, HNP, and IGES. Examples of suitable wheat varieties include Pavon, Anza, Chris, Coker 983, FLA301, FLA302, Fremont and Hunter.

Having identified the cereal plant of interest, plant cells suitable for transformation include immature embryos, calli, suspension cells, and protoplasts. It is particularly preferred to use suspension cells and immature embryos.

These cereal plant cells are transformed with a nucleic acid, which could be RNA or DNA and which is preferably cDNA, encoding a late embryogenesis abundant protein (LEA protein). The nucleic acid can be biologically isolated or synthetic. In the following Examples, the LEA protein is encoded by the HVA1 gene of barley, having the nucleotide and amino acid sequences as disclosed in Straub et al. (1994). However, other LEA genes can also be utilized, particularly other LEA genes belonging to group 3. These other group 3 LEA genes include cotton D-7 and D-29 (Baker et al., 1988; Dure et al., 1981), Brassica pLEA76 (Harada et al., 1989), carrot Dc8 and Dc3 (Franz et al., 1989; Seffens et al., 1990), soybean pmGM2 (Hsing et al., 1992), and wheat pMA2005 and pMA1949 (Curry et al., 1991; Curry and Walker-Simmons, 1991). The published nucleotide and amino acid sequences of each of these LEA proteins are hereby incorporated by reference. Each of these sequences can be used as the nucleic acid encoding an LEA protein to transform a suitable cereal plant according to the subject invention. Other LEA genes of group 2 or group 1 can also be used. Various LEA genes are disclosed in Dure (1992).

Transformation of plant cells can be accomplished by using a plasmid. The plasmid is used to introduce the nucleic acid encoding the LEA protein into the plant cell. Accordingly, a plasmid preferably includes DNA encoding the LEA protein inserted into a unique restriction endonuclease cleavage site. Heterologous DNA, as used herein, refers to DNA not normally present in the particular host cell transformed by the plasmid. DNA is inserted into the vector using standard cloning procedures readily known in the art. This generally involves the use of restriction enzymes and DNA ligases, as described by Sambrook et al., *Molecular Cloning: A Laboratory Manual,* 2d edition, Cold Spring Harbor Laboratory Press, Cold Spring Harbor, N.Y. [1989]. The resulting plasmid which includes nucleic acid encoding an LEA protein can then be used to transform a host cell, such as an Agrobacterium and/or a plant cell. (See generally, *Plant Molecular Biology Manual,* 2nd Edition, Gelvin, S. B. and Schilperoort, R. A., Eds., Kluwer Academic Press, Dordrecht, Netherlands (1994).)

For plant transformation, the plasmid preferably also includes a selectable marker for plant transformation. Commonly used plant selectable markers include the hygromycin phosphotransferase (hpt) gene, the phosphinothricin acetyl transferase gene (bar), the 5-enolpyruvylshikimate-3-phosphate synthase (EPSPS), neomycin 3'-O-phosphotransferase (npt II), or acetolactate synthase (ALS).

The plasmid preferably also includes suitable promoters for expression of the nucleic acid encoding the LEA protein and for expression of the marker gene. The cauliflower mosaic virus 35S promoter is commonly used for plant transformation, as well as the rice actin 1 gene promoter. In plasmid pBY520 used in the following examples, the nucleic acid encoding the LEA protein is under the control of the constitutive rice actin 1 gene promoter and the marker gene (bar) is under control of the cauliflower mosaic virus 35S promoter. Other promoters useful for plant transformation with the LEA gene include those from the genes encoding ubiquitin and proteinase inhibitor II (PINII), as well as stress-induced promoters (such as the HVA1 gene promoter of barley).

The plasmid designated pBY520 has been deposited in *Escherichia coli* strain pBY520/DH5α pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 69930 on Oct. 12, 1995.

For plant transformation, the plasmid also preferably includes a nucleic acid molecule encoding a 3' terminator such as that from the 3' non-coding region of genes encoding a proteinase inhibitor, actin, or nopaline synthase (nos).

Other suitable plasmids for use in the subject invention can be constructed. For example, LEA genes other than the HVA1 gene of barley could be ligated into plasmid pBY520 after use of restriction enzymes to remove the HVA1 gene. Other promoters could replace the actin 1 gene promoter present in pBY520. Alternatively, other plasmids in general containing LEA genes under the control of a suitable promoter, with suitable selectable markers, can be readily constructed using techniques well known in the art.

Having identified the plasmid, one technique of transforming cereal plant cells with a gene which encodes for an LEA protein is by contacting the plant cell with an inoculum of a bacteria transformed with the plasmid comprising the gene that encodes for the LEA protein. Generally, this procedure involves inoculating the plant cells with a suspension of the transformed bacteria and incubating the cells for 48 to 72 hours on regeneration medium without antibiotics at 25–28° C.

Bacteria from the genus Agrobacterium can be utilized to transform plant cells. Suitable species include *Agrobacterium tumefaciens* and *Agrobacterium rhizogenes. Agrobacterium tumefaciens* (e.g., strains LBA4404 or EHA105) is particularly useful due to its well-known ability to transform plants.

In inoculating the cells of cereal plants with Agrobacterium according to the subject invention, the bacteria must be transformed with a vector which includes a gene encoding for an LEA protein.

Plasmids, suitable for incorporation in Agrobacterium, which include a gene encoding for an LEA protein, contain an origin of replication for replication in the bacterium *Escherichia coli*, an origin of replication for replication in the bacterium *Agrobacterium tumefaciens*, T-DNA right border sequences for transfer of genes to plants, and marker genes for selection of transformed plant cells. Particularly preferred is the vector pBI121 which contains a low-copy RK2 origin of replication, the neomycin phosphotransferase (nptII) marker gene with a nopaline synthase (NOS) promoter and a NOS 3' polyadenylation signal. T-DNA plasmid vector pBI121 is available from Clonetech Laboratories, Inc., 4030 Fabian Way, Palo Alto, Calif. 94303. A gene encoding for an LEA protein is inserted into the vector to replace the beta-glucuronidase (GUS) gene.

Typically, Agrobacterium spp. are transformed with a plasmid by direct uptake of plasmid DNA after chemical and heat treatment, as described by Holsters et al. (1978); by direct uptake of plasmid DNA after electroporation, as described by S. Wen-jun and B. Forde, (1989); by triparental conjugational transfer of plasmids from *Escherichia coli* to Agrobacterium mediated by a Tra+ help strain as described by Ditta et al. (1981); or by direct conjugational transfer from *Escherichia coli* to Agrobacterium as described by Simon et al. (1982).

Another method for introduction of a plasmid containing nucleic acid encoding an LEA protein into a plant cell is by transformation of the plant cell nucleus, such as by particle bombardment. As used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the heterologous DNA. Alternatively, the target cell can be surrounded by the plasmid so that the plasmid is carried into the cell by the wake of the particle. Biologically active particles (e.g., dried bacterial cells containing the plasmid and heterologous DNA) can also be propelled into plant cells.

A further method for introduction of the plasmid into a plant cell is by transformation of plant cell protoplasts (stable or transient). Plant protoplasts are enclosed only by a plasma membrane and will therefore take up macromolecules like heterologous DNA. These engineered protoplasts can be capable of regenerating whole plants. Suitable methods for introducing heterologous DNA into plant cell protoplasts include electroporation and polyethylene glycol (PEG) transformation. As used throughout this application, electroporation is a transformation method in which, generally, a high concentration of plasmid DNA (containing heterologous DNA) is added to a suspension of host cell protoplasts and the mixture shocked with an electrical field of 200 to 600 V/cm. Following electroporation, transformed cells are identified by growth on appropriate medium containing a selective agent.

As used throughout this application, transformation encompasses stable transformation in which the plasmid is integrated into the plant chromosomes.

In the Examples which follow, rice has been transformed using biolistic transformation. Other methods of transformation have also been used to successfully transform rice plants, including the protoplast method (for a review, see Cao et al., 1992), and the Agrobacterium method (Hiei et al., 1994). Biolistic transformation has also been used to successfully transform maize (for a review, see Mackey et al., 1993) and wheat (see U.S. Pat. No. 5,405,765 to Vasil et al.).

Once a cereal plant cell or protoplast is transformed in accordance with the present invention, it is regenerated to form a transgenic cereal plant. Generally, regeneration is accomplished by culturing transformed cells or protoplasts on medium containing the appropriate growth regulators and nutrients to allow for the initiation of shoot meristems. Appropriate antibiotics are added to the regeneration medium to inhibit the growth of Agrobacterium or other contaminants and to select for the development of transformed cells or protoplasts. Following shoot initiation, shoots are allowed to develop in tissue culture and are screened for marker gene activity.

In suitable transformation methods, the cereal plant cell to be transformed can be in vitro or in vivo, i.e. the cereal plant cell can be located in a cereal plant.

The invention also provides a transgenic cereal plant produced by the method of the subject invention, as well as seed produced by the transgenic cereal plant.

The invention further provides a cereal plant cell or protoplast or a transgenic cereal plant transformed with a nucleic acid encoding a late embryogenesis abundant protein that confers water stress or salt stress tolerance to the plant generated from the cereal plant cell or protoplast or to the transgenic cereal plant. As discussed above, various cereal plants and LEA genes can be utilized.

Preferably, the nucleic acid encoding an LEA protein is controlled by a strong promoter to effect maximum expression of the LEA protein, or by a stress-induced promoter to effect induction of the promoter in response to stress conditions. In one embodiment, the transgenic cereal plant cell or protoplast or plant is transformed with the nucleic acid encoding the promoter, such as the rice actin 1 gene promoter, by providing a plasmid which includes DNA encoding the LEA gene and the promoter.

The transgenic cereal plant cell or protoplast or plant can also be transformed with a nucleic acid encoding a selectable marker, such as the bar gene, to allow for detection of transformants, and with a nucleic acid encoding the cauliflower mosaic virus 35S promoter to control expression of the bar gene. Other selectable markers include genes encoding EPSPS, nptII, or ALS. Other promoters include those from genes encoding actin 1, ubiquitin, and PINII. These additional nucleic acid sequences can also be provided by the plasmid encoding the LEA gene and its promoter. Where appropriate, the various nucleic acids could also be provided by transformation with multiple plasmids.

The invention is also directed to a transgenic cereal plant regenerated from the transgenic cereal plant cells or protoplasts, as well as to seed produced by the transgenic cereal plants. The invention is also directed to seed, which upon germination, produces the transgenic cereal plant.

While the nucleotide sequence referred to herein encodes an LEA protein, nucleotide identity to a previously sequenced LEA protein is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the LEA protein nucleotide and/or amino acid sequences which have minimal influence on the properties, secondary structure, and hydrophilic/hydrophobic nature of the encoded LEA protein. These variants are encompassed by the nucleic acid encoding an LEA protein according to the subject invention.

Also encompassed by the present invention are transgenic cereal plants transformed with fragments of the nucleic acids encoding the LEA proteins of the present invention. Suitable fragments capable of conferring water stress or salt stress tolerance to cereal plants can be constructed by using appropriate restriction sites. A fragment refers to a continuous portion of the LEA encoding molecule that is less than the entire molecule.

Non-essential nucleotides could be placed at the 5' and/or 3' end of the fragments (or the full length LEA molecules) without affecting the functional properties of the fragment or molecule (i.e. in increasing water stress or salt stress tolerance). For example, the nucleotides encoding the protein may be conjugated to a signal (or leader) sequence at the N-terminal end (for example) of the protein which co-translationally or post-translationally directs transfer of the protein. The nucleotide sequence may also be altered so that the encoded protein is conjugated to a linker or other sequence for ease of synthesis, purification, or identification of the protein.

Materials and Methods

Construction of Act1-HVA1 Plasmid for Rice Transformation

A 1.0-kb EcoRI fragment containing the full-length HVA1 cDNA was isolated from the cDNA clone pHVA1 (Hong et al., 1988), and this fragment was blunted with Klenow DNA polymerase and subcloned into the SmaI site of the plasmid expression vector pBY505, which is a derivative of pBluescriptIIKS(+)(Stratagene, Calif.), to create pBY520. On pBY520, the HVA1 structural gene is regulated by rice actin 1 gene (Act1) promoter (McElroy et al., 1990; Zhang, et al, 1991) and is between the Act1 promoter and the potato proteinase inhibitor II gene (Pin2) 3' region (Thornburg et al., 1987). Plasmid pBY520 also contains the bacterial phosphinothricin acetyl transferase (PAT) structural gene (commonly known as bar gene) (White et al., 1990), which serves as the selectable marker in rice transformation by conferring resistance to phosphinothricin-based herbicides. The bar gene is regulated by the cauliflower mosaic virus (CaMV) 35S promoter and followed by the nopaline synthase gene (nos) termination signal. Plasmid pBY520 has been deposited with the ATCC under Accession No. 69930.

Production of Transgenic Rice Plants

Calli were induced from immature embryos of rice (*Oryza sativa* L c.v. Nipponbare; available from the International Rice Research Institute, Los Banos, Philippines) and suspension cultures were established from selected embryogenic calli after three months of subculture in liquid medium. Fine suspension culture cells were used as the transformation material and bombarded with tungsten particles coated with the pBY520 plasmid as described by Cao et al. (1992). Resistant calli were selected in selection medium containing 6 mg/l of ammonium glufosinate (Crescent Chemical Co., Hauppauge, N.Y.) as the selective agent for 5–7 weeks. The resistant calli were transferred to MS (Murashige and Skoog, 1962) regeneration medium containing 3 mg/l of ammonium glufosinate to regenerate into plants. Plants regenerated from the same resistant callus were regarded as clones of the same line. Regenerated plants were transferred into soil and grown in the greenhouse (32° C. day/22° C. night, with a supplemental photoperiod of 10 h).

Herbicide-Resistance Test of Transgenic Rice Plants

The presence of the transferred genes in regenerated rice plants was first indicated by herbicide resistance of the plants. For the herbicide-resistance test, a water solution containing 0.5% (V/V) commercial herbicide BASTA™ (containing 162 g/l glufosinate ammonium, Hoechst-Roussel Agri-Vet Company, Somerville, N.J.) and 0.1% (V/V) Tween-20 was painted on both sides of a leaf. After one week, the resistant/sensitive phenotype was scored. Treated leaves of nontransformed (NT) plants were severely damaged or died, whereas the treated leaves of transgenic plants were not affected or only slightly damaged in the treated areas.

DNA Blot Hybridization Analysis of Transgenic Rice Plants

Integration of the transferred genes (including HVA1) into the rice genome of the first generation ($R_0$) transgenic rice plants was confirmed by DNA blot hybridization analysis using the HVA1 coding region as the probe. Genomic DNA was isolated as described by Zhao et al. (1989). For DNA blot hybridization analysis, 10 to 15 µg of DNA from each sample was digested with restriction endonuclease HindIII, or a combination of EcoRI and BamHI, separated on a 1.0% agarose gel, transferred onto a nylon membrane, and hybridized with the $^{32}$P-labeled HVA1 probe as shown in FIG. 1. There is a single HindIII site on the plasmid, thus digestion of genomic DNA with HindIII releases the fusion fragment containing the HVA1 sequence and rice genomic sequence. Digestion with EcoRI and BamHI releases the 1.0-kb fragment containing the HVA1 cDNA.

Immunoblot Analysis of HVA1 Protein Production in Transgenic Rice Plants

Protein extracts were prepared by grinding plant tissue in liquid nitrogen and homogenizing in extraction buffer containing 50 mM sodium phosphate (pH 7.0), 10 mM EDTA, 0.1% (V/V) Triton X-100, 0.1% (W/V) Sarkosyl, 10 mM β-mercaptoethanol, and 25 mg/ml phenylmethylsulfonyl fluoride. Mature seeds were cut into two halves, and the embryo-containing half-seeds were directly ground into fine powder and homogenized in the same extraction buffer. The homogenates were centrifuged at 5,000×g for 5 min at room temperature. The supernatants were further clarified by centrifugation at 12,000×g for 15 min at 4° C. The protein concentrations were determined based on the method of Bradford (1976) using a dye concentrate from BioRad (Hercules, Calif.). Proteins were separated by SDS-PAGE mini-gels, transferred electrophoretically to PVDF membrane using Mini Trans-Blot Cells (BioRad), blocked with 3% (W/V) BSA in TBS containing 0.05% (V/V) Triton X-100, incubated with rabbit anti-HVA1 antibody, and then incubated with goat anti-rabbit IgG alkaline phosphatase conjugate (BioRad). Secondary antibody was detected using 4-nitroblue-tetrazolium chloride (NBT) and 5-bromo-4-chloro-3-indolyl-phosphate (BCIP) supplied in an alkaline phosphatase immunoassay kit from BioRad. Immunoreaction signals on the blot filters were scanned using a densitometer (Helena Laboratories, Beaumont, Tex.) to quantify the relative amounts of the HVA1 protein. Partially purified HVA1 protein was used as the standard to estimate the levels of HVA1 protein in transgenic rice tissues.

Analysis of Growth Performance of Transgenic Plants under Drought- and Salt-Stress Conditions Evaluation of the growth performance under drought- and salt-stress conditions was carried out using the second generation ($R_1$) plants. These $R_1$ plants represent a population that include homozygous and heterozygous transgenic plants and segregated nontransgenic plants. Seeds of either wild-type rice plants or transformation procedure-derived nontransformed (NT) plants were used as control materials. They are both referred to as nontransformed control plants throughout this specification.

Seed Germination and Seedling Growth in Medium

Thirty $R_1$ seeds from each of three transgenic rice lines and two nontransformed control plants were surface-sterilized and germinated in the dark at 25° C. on three kinds of agarose media: MS, MS+100 mM NaCl, and MS+200 mM mannitol. The MS medium contains only its mineral salts. Seeds were allowed to germinate in MS+100 mM NaCl or MS+200 mM mannitol for 5 d and subsequently transferred to MS medium. To test the response of young seedlings to stress conditions, seeds were germinated in MS medium for 5 d. The 5-d-old seedlings were then divided, transferred onto two layers of Whatman paper in deep petri dishes and supplied with liquid MS, MS+100 mM NaCl, and MS+200 mM mannitol, respectively. Seedlings were grown under light at 25° C. and their response to the stress conditions was monitored for 5 d.

Growth and Stress Treatments of Plants in Soil

Refined and sterilized field soil supplemented with a composite fertilizer was used to grow rice plants in the greenhouse (32° C. day/22° C. night, with a supplemental photoperiod of 10 h). This growth condition has been routinely used to support normal growth of several rice varieties. Seeds were germinated in MS medium for 7 d, and the 7-d-old seedlings were transferred into soil in small pots with holes on the bottom (8 cm×8 cm, one plant per pot). The pots were kept in flat-bottom trays containing water. The seedlings were grown for two additional weeks before they were exposed to stress treatments. At this stage, most of the 3-week-old seedlings had three leaves, and some seedlings had an emerging fourth leaf. Two stress experiments using different sets of $R_1$ plants from the same $R_1$ transgenic line were conducted. In each experiment, 10 transgenic plants and at least 10 nontransformed control plants were used for each treatment.

(i) Non-stress: The plants were supplied with water continuously from the trays. The nontreated plants were also measured for their growth when the stressed plants were measured. Under this condition, both the transgenic plants and the nontransformed control plants grew well and did not show any significant difference in their growth performance during the entire period of experiments.

(ii) Water-stress: To start drought stress, water was withheld from the trays. The gradual but rapid decrease of water content in the soil produced a drought situation. After 5 d drought stress, the plants were re-supplied with water for 2 d to allow the wilted plants to recover. Then, the second round of water stress was carried out.

(iii) Salt-stress: Short-term severe salt-stress in the soil was produced by transferring the pots into trays containing 200 mM NaCl solution for 10 d. Then, the pots were transferred back to trays containing tap water to let the plants recover for 10 d. Salt concentration in the soil was quickly reduced by flushing the soil in the pots from the top with water and changing the water in the trays for several times during the first 2 d. A second round of salt stress was imposed after 10 d of recovery by supplying the plants with 50 mM NaCl solution for 30 d.

Data Collection and Statistical Analysis of Growth Performance

Before starting stress treatments, each nontransformed control plant and transgenic plant was measured for its initial height, leaf number and length. During and after stress treatments, each plant was also measured. For statistical analysis, the mean value of the tested plants in each treatment was calculated and used for comparing the transgenic plants with the nontransformed control plants.

EXAMPLE 1

Production and Molecular Analysis of Transgenic Rice Plants

The structure of the plasmid pBY520 is shown in FIG. 1. The cDNA of the barley LEA gene, HVA1, is located downstream of the rice actin 1 gene (Act1) promoter. The coding region of the bacterial phosphinothricin acetyl transferase gene (bar) is located downstream of the cauliflower mosaic virus (CaMV) 35S promoter. Rice suspension cells, which were supported by filter papers and precultured in solid medium, were bombarded by tungsten particles coated with the plasmid DNA pBY520. Results of three transformation experiments are summarized in Table I. Thirty-three plates of suspension cells were bombarded in these transformation experiments. Two hundred ammonium glufosinate-resistant calli were selected and transferred onto regeneration medium. Sixty-three independent lines of plants (120 plants) were regenerated and grown in the greenhouse. As shown in Table I, more than 85% of the transgenic plants are fertile, producing various numbers of seeds. The sterility of some transgenic lines appeared unrelated to the presence of the foreign genes, since similar percentages of sterile plants were obtained in parallel experiments where the suspension cells were bombarded without plasmid DNA or with several other gene constructs.

Phosphinothricin acetyl transferase encoded by the bar gene can detoxify phosphinothricin-based herbicides. Twenty-nine lines of plants were first tested for herbicide resistance. When painted with 0.5% commercial herbicide BASTA™, leaves of transgenic plants showed complete resistance, whereas the leaves of nontransformed plants turned yellow and died. Among 29 lines of plants that were tested for herbicide resistance, 90% of them were resistant. The same 29 lines were further analyzed by DNA blot hybridization using the HVA1 cDNA fragment as probe, and 80% of them showed the predicted hybridization band pattern.

Digestion of plasmid pBY520 or genomic DNA from transgenic rice plants releases the 1.0-kb fragment containing the HVA1 coding region. Among 29 lines analyzed, 23 of them contained the expected 1.0-kb hybridization band. The hybridization patterns of all transgenic plants are unique except the predicted 1.0-kb hybridization band, suggesting that these transgenic lines were from independent transformation events. Results of DNA blot hybridization are generally consistent with those of herbicide resistance test, therefore both the selectable marker gene and the HVA1 gene on the same plasmid were efficiently co-integrated into the rice genome. The use of a plasmid containing both the selectable gene and the HVA1 gene in conjunction with the tight selection procedure contributed to the high efficiency of regenerating transgenic plants.

EXAMPLE 2

Analysis of Accumulation of HVA1 Protein in $R_0$ Transgenic Rice Plants

The accumulation of HVA1 protein in a number of first generation ($R_0$) transgenic lines, which were selected based on the DNA blot hybridization data, was analyzed. Protein extracts were prepared from both leaf and root tissues. The HVA1 protein was detected by a polyclonal antibody raised against purified barley HVA1 protein. A single band of 27 kD in SDS-PAGE gel, which corresponds to the HVA1 protein, was detected in the leaf tissue of different transgenic lines. Accumulation of HVA1 protein was also readily detected in roots, although the levels were relatively low compared with the levels in the leaf tissues. The relative levels of accumulation of the HVA1 protein in roots correspond to those in leaf tissue among different transgenic lines. Protein extracts of nontransformed plants did not show the 27-kD protein band, and there were no additional bands of other sizes detected in the protein extracts of the transgenic plants or the nontransformed plants. Using a partially purified HVA1 protein preparation as standard, the levels of HVA1 protein accumulated in the leaf and root tissues of different transgenic lines were estimated to be in the range of 0.3–2.5% of the total soluble proteins (Table II).

To detect HVA1 protein accumulation in mature transgenic rice seeds, especially in the embryos, protein extracts were also prepared from embryo-containing half-seeds and analyzed by immunoblot. The 27-kD band corresponding to the HVA1 protein was not detected in the protein extracts of mature transgenic seeds. However, two strong bands with lower molecular mass, 20 kD and 13 kD respectively, were detected. Since a high-level mRNA transcript highly homologous to the barley HVA1 gene has already been detected in mature rice seeds in a previous study (Hong et al., 1992), these two proteins may represent endogenous rice LEA or LEA-like proteins accumulated during the late stage of seed development. The lack of HVA1 protein accumulation in mature transgenic rice seeds may be due to the low (or lack of) activity of the Act1 promoter after seeds start to desiccate.

EXAMPLE 3

Increased Tolerance to Drought- and Salt-Stress of Transgenic Rice Plants

Results described above demonstrated that expression of the barley HVA1 gene regulated by the strong rice Act1 promoter leads to high-level accumulation of the HVA1 protein in vegetative tissues of transgenic rice plants. Most of the primary transgenic rice plants appeared morphologically normal compared with transformation procedure-derived nontransformed plants or wild-type plants. As described earlier, most plants are fertile. Taken together, these results suggest that accumulation of HVA1 protein does not have detrimental effects on the growth and development of rice plants.

To determine whether the high-level accumulation of the HVA1 protein would have any beneficial effect on the growth performance of transgenic rice plants under stress conditions, evaluation of the growth performance under water- and salt-stress conditions was carried out using the second generation ($R_1$) plants. Seeds of wild-type rice plants or seeds of transformation procedure-derived nontransformed plants were used as controls.

Seed Germination and Seedling Growth in Medium under Osmotic and Salt Stress Conditions In MS medium, seeds from both transgenic and control plants germinated well, and no difference was observed in their seedling growth. In MS+100 mM NaCl or MS+200 mM mannitol, both transgenic seeds and control seeds germinated slowly (2 d delay for emergence of the shoot and root), but no difference was observed between transgenic and control seeds. After 5 d in the two stress media, the germinating seeds (with 0.2–0.5 cm long shoot) were transferred onto MS medium. Both transgenic and control seedlings recovered and resumed normal growth. However, transgenic seedlings grew faster during this recovery period, and the shoots of transgenic seedlings were significantly longer than those of the control seedlings after one week. Transgenic seedlings also had 1 to 3 more adventitious roots than the control seedlings. No significant difference was observed between nontransformed control plants and transgenic plants when seeds were germinated and grown continuously in MS medium (Table III).

Five-day-old seedlings from seeds germinated in MS medium were tested for their response to salt-stress. Both the transgenic and control seedlings were very sensitive to salt stress. In MS+100 mM NaCl, the seedlings gradually wilted within one week. However, the wilting of transgenic seedlings was delayed compared to the control seedlings. During the first three days in MS+100 mM NaCl, more than half of the control seedlings became wilted., but only a very few transgenic seedlings became wilted.

Growth Performance of Transgenic Plants in Soil under Water-Stress (Drought) Conditions The above experiments showed that transgenic plants and control plants respond to stress treatments differently. Extensive stress experiments were conducted using 3-week-old plants grown in the soil. Under constant nonstress condition in soil, no significant differences were observed between transgenic plants and control plants in their growth performance during the entire period of the experiment.

Upon withholding water from the trays, the gradual but rapid decrease of water content in the soil created a drought condition. There is a significant difference between the transgenic plants and the control plants in their response to this drought condition. Leaves at the same developmental stage of the transgenic plants became wilted about 1 to 2 d later than that of the control plants. After 4 to 5 d of drought stress, leaves of both control and transgenic plants became wilted, but wilting of transgenic plants was considerably less severe. The difference between transgenic and control plants in response to water deficit was also reflected in their growth rate of young leaves (increase of leaf length) during the first 3 d of drought stress. Drought stress inhibited the growth of the young leaves of control plants as well as transgenic plants. However, transgenic plants maintained higher growth rate than control plants (Table IV). After the drought-stressed plants were rewatered, the transgenic plants showed better recovery and resumed faster growth than the control plants. Transgenic plants are less damaged by the drought stress and look much healthier, whereas old leaves and tips of young leaves of nontransformed plants (NT) showed poor recovery and gradually died.

Data in Table IV show the average plant height and root fresh weight of the stressed plants after four cycles of 5-d drought stress followed by 2-d recovery with watering. In summary, transgenic plants showed significant advantages over control plants in their growth performance under drought-stress conditions. The growth advantage was particularly evident in the growth of roots.

Growth Performance of Transgenic Plants in Soil under Salt Stress Conditions

Severe salt stress (200 mM NaCl) significantly inhibited the growth of both transgenic and control plants, although the plants did not become wilted as quickly as those plants under drought stress. However, transgenic plants maintained much higher growth rate than the control plants at early stage (d 0 to d 5) of salt-stress (Table V). Early symptoms of damage due to salt-stress, such as wilting, bleaching, and death of leaf tips, occurred first in old leaves. Leaves at the bottom of a plant became wilted or died first. At the later stage, the young leaves developed necrosis symptoms and started to wilt and dry from the leaf tips. Again, appearance and development of these symptoms occurred much more slowly in transgenic plants than in control plants. When the two leaves at the bottom of most control plants became wilted, the first leaf at the bottom of most transgenic plants showed only slight wilting. Wilting of young leaves of transgenic plants was always less severe compared with the control plants. Upon removal of the salt stress, transgenic plants showed much better recovery than the nontransformed control plants. Data in Table V also show the average shoot height and root fresh weight of the stressed plants 30 d after the initial salt-stress treatment. Again, transgenic plants showed significantly better performance than the control plants under extended stress condition. Under continuous severe salt stress, most of the nontransformed plants gradually died, whereas most transgenic plants survived a much longer time.

EXAMPLE 4

Analysis of Accumulation of HVA1 Protein in $R_1$ Transgenic Rice Plants

HVA1 protein accumulation was analyzed in $R_1$ plants from two $R_0$ transgenic lines at the end of the stress experiment. Eight $R_1$ plants from each $R_0$ transgenic lines were analyzed. In each line, HVA1 protein was not detected in two out of eight $R_1$ plants, and this is due to the segregation of the transferred gene in these second-generation plants. Those $R_1$ plants that lacked HVA1 protein accumulation were severely inhibited and damaged by the stress treatments. These plants showed poor recovery after the first period of salt stress and gradually died under continuous stress condition. HVA1 protein accumulation was detected in all the surviving $R_1$ transgenic plants that showed tolerance to stress.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE I

Summary of transformation experiments

| Transformation Experiment | No. of Plates of Cells Bombarded | No. of Resistant Calli Selected | No. of Lines (Plants) Regenerated | No. of Fertile Lines (%) |
|---|---|---|---|---|
| 1 | 8 | 107 | 27 (67) | |
| 2 | 15 | 69 | 15 (27) | |
| 3 | 10 | 24 | 21 (26) | |
| Total | 33 | 200 | 63 (120) | 54 (86) |

TABLE II

Estimated levels of HVA1 protein accumulation in different transgenic lines

| | Level of HVA1 Protein Accumulation (% of Total Soluble Proteins) | |
|---|---|---|
| Transgenic Line ($R_0$) | Leaf | Root |
| NT | 0 | 0 |
| 3 | 1.00 | ND |
| 13 | 0.75 | ND |
| 18 | 2.50 | ND |
| 19 | 0.60 | 0.30 |
| 30 | 0.50 | 0.30 |
| 36 | 1.50 | 1.00 |
| 38 | 0.80 | 0.60 |
| 41 | 1.00 | 0.70 |
| 61 | 0.75 | ND |

ND, not determined.

TABLE III

Seed germination and growth of young seedlings in medium under osmotic stress or salt stress

| | Length of Shoot (cm) | | |
|---|---|---|---|
| Transgenic Line | MS | MS + mannitol | MS + NaCl |
| NT | 7.5 ± 0.2 | 4.2 ± 0.2 (100) | 2.7 ± 0.2 (100) |
| 30 | 7.3 ± 0.2 | 5.2 ± 0.2 (124) | 3.5 ± 0.2 (130) |
| 36 | 7.4 ± 0.2 | 6.1 ± 0.2 (145) | 4.9 ± 0.2 (181) |
| 41 | 7.7 ± 0.2 | 5.9 ± 0.2 (140) | 4.0 ± 0.2 (148) |

Data were collected 12 d after seed germination: 5 d in stress medium (MS + 200 mM mannitol or MS + 100 mM NaCl) and 7 d in nonstress medium (MS). Each value ± SE represents the average of 10 seedlings. For nonstress control, seeds were germinated and grown continuously in MS medium for 12 d. Numbers in parentheses are the percentage of shoot length of transgenic seedlings compared to control seedlings which was taken as 100.

TABLE IV

Growth performance of transgenic rice plants in soil under water-stress (drought) condition

| Transgenic Line | Leaf Growth Rate (% Length Increase)[a] | Plant Height (cm)[b] | Root Fresh Wt (g)[b] |
|---|---|---|---|
| NT | 69 | 22 ± 1.4 (100) | 0.9 ± 0.1 (100) |
| 30 | 90 | 29 ± 1.1 (132) | 1.4 ± 0.1 (156) |
| 36 | 129 | 37 ± 1.8 (168) | 2.1 ± 0.1 (233) |
| 41 | 113 | 33 ± 1.8 (150) | 2.3 ± 0.3 (256) |

[a]The lengths of the two upper leaves were measured before and 3 d after withholding water from the trays. Growth rate was calculated as percentage length increase of the two leaves during the 3-d period of drought stress.
[b]Data were collected at 28 d after the beginning of initial water stress (four cycles of 5-d drought stress followed by 2-d recovery with watering). The mean length of the two longest leaves on the top of the plants was used as a measure of the plant height. Each value ± SE represents the average of 10 plants except for root fresh weight which is the average of four plants. Numbers in parentheses are the percentage of transgenic plants compared to control plants which was taken as 100.

TABLE V

Growth performance of transgenic rice plants in soil under salt-stress condition

| Transgenic Line | Leaf Growth Rate (% Length Increase)[a] | Plant Height (cm)[b] | Root Fresh Wt (g)[b] | Number of surviving plants[c] |
|---|---|---|---|---|
| NT | 76 | 19 ± 1.1 (100) | 1.2 ± 0.1 (100) | 0 |
| 30 | 90 | 23 ± 0.9 (121) | 1.9 ± 0.1 (158) | 6 |
| 36 | 103 | 29 ± 0.8 (153) | ND | 8 |
| 41 | 115 | 26 ± 0.8 (137) | 2.6 ± 0.1 (217) | 8 |

[a]The lengths of the two upper leaves were measured before salt-stress, and at 5 d after salt-stress condition was imposed. Growth rate was calculated as percentage length increase of the two leaves during the 5-d period of salt stress.
[b]Data were collected at 30 d after beginning of the initial salt-stress (10 d in 200 mM NaCl, 10 d in tap water for recovery, and 10 d in 50 mM NaCl). The mean length of the two longest leaves on the top of the plants was used as a measure of the plant height. Each value ± SE represents the average of 10 plants except for root fresh weight which is the average of four plants. Numbers in parentheses are the percentage of transgenic plants compared to control plants which was taken as 100. ND, not determined.
[c]Data were collected from a second stress experiment at 40 d after beginning of the initial salt stress (10 d in 200 mM NaCl, 10 d in tap water for recovery, and 20 d in 50 mM NaCl). Ten transgenic plants from each transgenic line and 10 nontransformed control plants were used. For NT, all ten plants died. For transgenic lines 36 and 41, eight out of ten plants survived.

LIST OF REFERENCES CITED

Akbar M, et al., Breeding for soil stress. In Progress in Rainfed Lowland Rice. International Rice Research Institute, Manila, Philippines, pp 263–272 (1986a).

Akbar M, et al., Genetics of salt tolerance in rice. In Rice Genetics. International Rice Research Institute, Manila, Philippines, pp 399–409 (1986b).

Baker J, et al., Sequence and characterization of 6 LEA proteins and their genes from cotton. Plant Mol Biol 11: 277–291 (1988).

Blackman S A, et al., Maturation proteins associated with desiccation tolerance in soybean. Plant Physiol 96: 868–874 (1991).

Blackman S A, et al., Maturation proteins and sugars in desiccation tolerance of developing soybean seeds. Plant Physiol 100: 225–230 (1992).

Bradford K J and Chandler P M, Expression of "dehydrin-like" proteins in embryos and seedlings of *Ziaania palus-*

*tris* and *Oryza sativa* during dehydration. Plant Physiol 99: 488–494 (1992).

Bradford M, A rapid and sensitive method for quantitation of microgram quantities of protein utilizing the principle of protein-dye binding. Anal Biochem 72: 248–254 (1976).

Cao J, et al., Regeneration of herbicide resistant transgenic rice plants following microprojectile-mediated transformation of suspension culture cells. Plant Cell Rep 11: 586–591 (1992).

Cao J, et al., Assessment of rice genetic transformation techniques. In *Rice Biotechnology* (Khush G S and Toenniessen, G H eds.). C.A.B. International, International Rice Research Institute, Manila, Philippines, pp. 175–198 (DATE?????).

Chandler PM and Robertson M, Gene expression regulated by abscisic acid and its relation to stress tolerance. Annu Rev Plant Physiol Plant Mol Biol 45: 113–141 (1994).

Close T J, et al., A view of plant dehydrins using antibodies specific to the carboxy terminal peptide. Plant Mol Biol 23: 279–286 (1993).

Curry J, et al., Sequence analysis of a cDNA encoding a group 3 LEA mRNA inducible by ABA or dehydration stress in wheat. Plant Mol Biol 16: 1073–1076 (1991).

Curry J and Walker-Simmons M K, Unusual sequence of group 3 LEA (II) mRNA inducible by dehydration stress in wheat. Plant Mol Biol 21: 907–912 (1993).

Danyluk J, et al., Differential expression of a gene encoding an acidic dehydrin in chilling sensitive and freezing tolerant gramineae species. FEBS Lett 344: 20–24 (1994).

Ditta G, et al., Broad Host Range DNA Cloning System for Gram-negative Bacteria: Construction of a Gene Bank of *Rhizobium meliloti*. Proc Natl Acad Sci USA 77: 7347–7351 (1981).

Dure L III, The LEA proteins of higher plants. In DPS Verma, ed, Control of Plant Gene Expression. CRC Press, Boca Raton, Fla., pp 325–335 (1992).

Dure L III, A repeating 11-mer amino acid motif and plant desiccation. Plant J 3: 363–369 (1993).

Dure L III, et al., Common amino acid sequence domains among the LEA proteins of higher plants. Plant Mol Biol 12: 475–486 (1989).

Dure L III, Developmental biochemistry of cottonseed embryogenesis and germination: Changing mRNA populations as shown in vitro and in vivo protein synthesis. Biochemistry 20: 4162–4168 (1981).

Epstein E, et al., Saline culture of crops: a genetic approach. Science 210: 399–404 (1980).

Franz G, et al., Molecular and genetic analysis of an embryonic gene, DC 8, from *Dacus carota* [L.]. Mol Gen Genet 218: 143–151 (1989).

Greenway H and Munns R, Mechanisms of salt tolerance in nonhalophytes. Annu Rev Plant Physiol 31: 149–190 (1980).

Harada J, et al., Unusual sequence of a abscisic acid-inducible mRNA which accumulates late in *Brassica napus* development. Plant Mol Biol 12: 395–401 (1989).

Hiei Y, et al., Efficient transformation of rice (*Oryza sativa* L.) mediated by Agrobacterium and sequence analysis of the boundaries of the T-DNA. The Plant Journal 6: 271–282 (1994).

Holmstrom K-O, et al., Production of the *Escherichia coli* betaine-aldehyde dehydrogenase, an enzyme required for the synthesis of the osmoprotectant glycine betaine, in transgenic plants. Plant J 6: 749–758 (1994).

Holsters M, et al., Transfection and Transformation of *Agrobacterium tumefaciens*. Mol Gen Genet 163: 181–187 (1978).

Hong B, Regulation of synthesis and potential function of an ABA- and stress-induced protein in barley. PhD thesis, Washington University, St Louis, Mo. (1991).

Hong B, et al., Developmental and organ-specific expression of an ABA- and stress-induced protein in barley. Plant Mol Biol 18: 663–674 (1992).

Hong B, et al., Cloning and characterization of a cDNA encoding a mRNA rapidly induced by ABA in barley aleurone layers. Plant Mol Biol 11: 495–506 (1988).

Hsing YC, et al., Nucleotide sequences of a soybean complementary DNA encoding a 50-kilodalton late embryogenesis abundant protein. Plant Physiol 99: 353–355 (1992).

Iturriaga G, et al., Expression of desiccation-related proteins from the resurrection plant *Craterostigma plantagineum* in transgenic tobacco. Plant Mol Biol 20: 555–558 (1992).

Mackey C. J. et al., Transgenic maize in *Transgenic Plants* (Kung S D and Wu R. eds), vol. 2, pp. 21–33 (1993).

McElroy D, et al., Isolation of an efficient actin promoter for use in rice transformation. The Plant Cell 2: 163–171 (1990).

Moons A, et al., Molecular and physiological responses to abscisic acid and salts in roots of salt-sensitive and salt-tolerant Indica rice varieties. Plant Physiol 107: 177–186 (1995).

Mundy J and Chua N-H, Abscisic acid and water stress induce the expression of novel rice gene. EMBO J 7: 2279–2286 (1988).

Murashige T and Skoog F, A revised medium for rapid growth and bioassays with tobacco tissue cultures. Physiol Plant 15: 473–497 (1962).

Pilon-Smits EAH, et al., Improved performance of transgenic fructan-accumulating tobacco under drought stress. Plant Physiol 107: 125–130 (1995).

Rathinasabapathi B, et al., Metabolic engineering of glycine betaine synthesis: plant betaine aldehyde dehydrogenases lacking typical transit peptides are targeted to tobacco chloroplasts where they confer betaine aldehyde resistance. Planta 193: 155–162 (1994).

Ried J L and Walker-Simmons M K, Group 3 late embryogenesis abundant proteins in desiccation-tolerant seedlings of wheat (*Triticum aestivum* L.). Plant Physiol 102: 125–131 (1993).

Roberts J K, et al., Cellular concentrations and uniformity of cell-type accumulation of two Lea proteins in cotton embryos. Plant Cell 5: 769–780 (1993).

Seffens W S, et al., Molecular analysis of a phylogenetically conserved carrot gene: developmental and environmental regulation. Devel Genet 11: 65–76 (1990).

Shen W and Forde B G, Efficient Transformation of Agrobacterium spp. by High Voltage Electroporation. Nucleic Acids Res 17: 8385 (1989).

Simon R, et al., A Broad Host Range Mobilization System for in vivo Genetic Engineering: Transposon Mutagenesis in Gram-negative Bacteria. Biotechnology 1: 784–791 (1982).

Skriver K and Mundy J, Gene expression in response to abscisic acid and osmotic stress. Plant Cell 2: 503–512 (1990).

Still D W, et al., Development of desiccation tolerance during embryogenesis in rice (*Oryza sativa*) and wild rice (*Zizania palustris*). Dehydrin expression, abscisic acid content, and sucrose accumulation. Plant Physiol 104: 431–438 (1994).

Straub P F, et al., Structure and promoter analysis of an ABA- and stress-regulated barley gene, HVA1. Plant Mol Biol 26: 617–630 (1994).

Tarczynski M C, et al., Stress protection of transgenic tobacco by production of the osolyte mannitol. Science 259: 508–510 (1993).

Thornburg R W, et al., Wound-inducible expression of a potato inhibitor II-chloramphenicol acetyl transferase gene fusion in transgenic tobacco plants. Proc Natl Acad Sci USA 84: 744–748 (1987).

White J et al., A cassette containing the bar gene of *Streptomyces hygroscopicas*: a selectable marker for plant transformation. Nucleic Acids Res 18: 1062 (1990).

Yancey P H, et al., Living with water stress: evolution of osmolyte system. Science 217: 1214–1222 (1982).

Yamaguchi-Shinozaki K, et al., Four tightly-linked rab genes are differentially expressed in rice. Plant Mol Biol 14: 29–39 (1989).

Zhang W G, et al., Analysis of rice Act1 5' region activity in transgenic rice plants. The Plant Cell 3: 1155–1165 (1991).

Zhao X, et al., Genomic-specific repetitive sequences in the genus Oryza. Theor Appl Genet 78: 201–209 (1989).

What is claimed is:

1. A method of producing a cereal plant cell or protoplast useful for regeneration of a water stress or salt stress tolerant cereal plant, said method comprising:

transforming a cereal plant cell or protoplast with nucleic acid encoding a group 3 late embryogenesis abundant protein.

2. The method of claim 1 wherein said cereal plant cell or protoplast is derived from a rice plant.

3. The method of claim 1 wherein said nucleic acid encoding a late embryogenesis abundant protein is the HVA1 gene of barley.

4. The method of claim 1 wherein said transformation comprises:

propelling particles at said cereal plant cell under conditions effective for the particles to penetrate the cell interior; and introducing a plasmid comprising the nucleic acid encoding the late embryogenesis abundant protein into the cell interior.

5. The method of claim 4 wherein the plasmid is associated with the particles, whereby the plasmid is carried into the cell or protoplast interior together with the particles.

6. The method of claim 4 wherein the plasmid is designated pBY520.

7. The method of claim 1 further comprising regenerating the transformed cereal plant cell or protoplast to form a transgenic cereal plant.

8. A transgenic cereal plant produced by the method of claim 7.

9. A seed produced by the transgenic cereal plant of claim 8.

10. A method of increasing tolerance of a cereal plant to water stress or salt stress conditions, said method comprising increasing levels of a late embryogenesis abundant protein by transforming the plant with a nucleic acid encoding a group 3 late embryogenesis abundant protein.

11. A cereal plant cell or protoplast transformed with a nucleic acid encoding a group 3 late embryogenesis abundant protein that confers water stress or salt stress tolerance on a cereal plant regenerated from said cereal plant cell or protoplast.

12. The cereal plant cell of claim 11 wherein said cereal plant cell or protoplast is derived from a rice plant.

13. The cereal plant cell or protoplast of claim 11 wherein said nucleic acid encoding a late embryogenesis abundant protein is the HVA1 gene of barley.

14. The cereal plant cell or protoplast of claim 11 wherein said cereal plant cell or protoplast includes a nucleic acid encoding a promoter, wherein expression of said nucleic acid encoding said late embryogenesis abundant protein is controlled by said promoter.

15. The cereal plant cell or protoplast of claim 14 wherein said promoter is the rice actin 1 gene promoter.

16. The cereal plant cell or protoplast of claim 11 wherein said cereal plant cell or protoplast includes a nucleic acid encoding a selectable marker.

17. The cereal plant cell or protoplast of claim 16 wherein said nucleic acid encoding a selectable marker is the bar gene.

18. The cereal plant cell or protoplast of claim 17 wherein said cereal plant cell or protoplast includes a nucleic acid encoding the cauliflower mosaic virus 35S promoter, wherein expression of said bar gene is controlled by the cauliflower mosaic virus 35S promoter.

19. A transgenic cereal plant regenerated from the cereal plant cell or protoplast of claim 11.

20. A seed produced by the transgenic cereal plant of claim 19.

21. A transgenic cereal plant transformed with a nucleic acid encoding a group 3 late embryogenesis abundant protein that confers water stress or salt stress tolerance to the plant.

22. The transgenic cereal plant of claim 21 wherein said cereal plant is a rice plant.

23. The transgenic cereal plant of claim 21 wherein said nucleic acid encoding a late embryogenesis abundant protein is the HVA1 gene of barley.

24. The transgenic cereal plant of claim 21 wherein said transgenic cereal plant includes a nucleic acid encoding a promoter, wherein expression of said nucleic acid encoding said late embryogenesis abundant protein is controlled by said promoter.

25. The transgenic cereal plant of claim 24 wherein said promoter is the rice actin 1 gene promoter.

26. The transgenic cereal plant of claim 21 wherein said transgenic cereal plant includes a nucleic acid encoding a selectable marker.

27. The transgenic cereal plant of claim 26 wherein said nucleic acid encoding a selectable marker is the bar gene.

28. The transgenic cereal plant of claim 27 wherein said transgenic cereal plant includes a nucleic acid encoding the cauliflower mosaic virus 35S promoter, wherein expression of said bar gene is controlled by the cauliflower mosaic virus 35S promoter.

29. A seed produced by the transgenic cereal plant of claim 21.

30. A seed, which upon germination, produces the transgenic cereal plant of claim 21.

31. A transgenic cereal plant transformed with a plasmid that confers water stress or salt stress tolerance to the cereal plant, said plasmid comprising:

first nucleic acid encoding a group 3 late embryogenesis abundant protein;

second nucleic acid encoding a promoter, said second nucleic acid located 5' to said first nucleic acid and said second nucleic acid controlling expression of said first nucleic acid;

third nucleic acid encoding a termination signal, said third nucleic acid located 3' to said first nucleic acid;

fourth nucleic acid encoding a selectable marker, said fourth nucleic acid located 3' to said third nucleic acid;

fifth nucleic acid encoding a promoter, said fifth nucleic acid located 5' to said fourth nucleic acid and 3' to said third nucleic acid, said fifth nucleic acid controlling expression of said fourth nucleic acid; and sixth nucleic acid encoding a termination signal, said, sixth nucleic acid located 3' to said fourth nucleic acid.

32. The transgenic cereal plant of claim 31 wherein said plasmid is designated pBY520.

* * * * *